United States Patent
Ries et al.

(10) Patent No.: US 7,601,033 B2
(45) Date of Patent: Oct. 13, 2009

(54) CONNECTOR ASSEMBLY WITH INTERNAL SEALS AND MANUFACTURING METHOD

(75) Inventors: Andrew J. Ries, Lino Lakes, MN (US); George Patras, Greenfield, MN (US); Thomas J. Olson, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 180 days.

(21) Appl. No.: 11/680,721

(22) Filed: Mar. 1, 2007

(65) Prior Publication Data
US 2008/0139031 A1 Jun. 12, 2008

Related U.S. Application Data

(63) Continuation-in-part of application No. 11/608,011, filed on Dec. 7, 2006.

(51) Int. Cl.
*H01R 13/504* (2006.01)
*A61N 1/375* (2006.01)

(52) U.S. Cl. .................................. 439/669; 607/37

(58) Field of Classification Search ................ 439/668, 439/669, 909; 607/37
See application file for complete search history.

(56) References Cited

U.S. PATENT DOCUMENTS

| | | | |
|---|---|---|---|
| 3,908,668 A | 9/1975 | Bolduc | |
| 4,226,244 A | 10/1980 | Coury et al. | |
| 4,934,367 A | 6/1990 | Daglow et al. | |
| 4,971,057 A | 11/1990 | Theres | |
| 5,070,605 A | 12/1991 | Daglow et al. | |
| 5,076,270 A | 12/1991 | Stutz, Jr. | |
| 5,431,695 A | 7/1995 | Wiklund et al. | |
| 5,669,790 A * | 9/1997 | Carson et al. | 439/668 |
| 6,574,508 B2 | 6/2003 | Zaouli et al. | |
| 6,817,905 B2 | 11/2004 | Zart et al. | |
| 6,980,863 B2 | 12/2005 | van Venrooij et al. | |
| 7,083,474 B1 | 8/2006 | Fleck et al. | |
| 7,239,916 B2 | 7/2007 | Thompson et al. | |
| 7,299,095 B1 * | 11/2007 | Barlow et al. | 607/37 |
| 2003/0163171 A1 | 8/2003 | Kast et al. | |
| 2004/0122481 A1 | 6/2004 | Tidemand et al. | |
| 2005/0033138 A1 | 2/2005 | Ries et al. | |
| 2005/0137642 A1 | 6/2005 | Zart et al. | |
| 2005/0149140 A1 | 7/2005 | Hansen et al. | |
| 2007/0202728 A1* | 8/2007 | Olson et al. | 439/248 |

FOREIGN PATENT DOCUMENTS

WO 2007101233 9/2007

OTHER PUBLICATIONS

International Search Report, PCT/US2007/086791, Jun. 5, 2008, 5 Pages.

* cited by examiner

*Primary Examiner*—Neil Abrams
(74) *Attorney, Agent, or Firm*—Carol F. Barry

(57) ABSTRACT

An implantable medical device connector assembly and method of manufacture include a molded, insulative shell having an inner surface forming a connector bore, a circuit member including a one or more traces extending through the shell; one or more conductive members positioned along the connector bore and electrically coupled to the traces; and sealing members positioned between the conductive members.

17 Claims, 10 Drawing Sheets

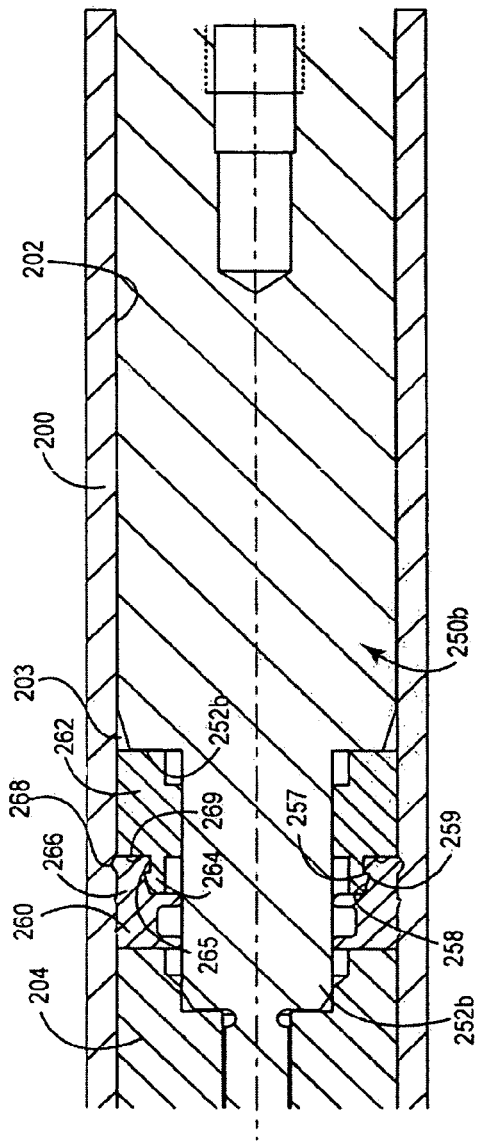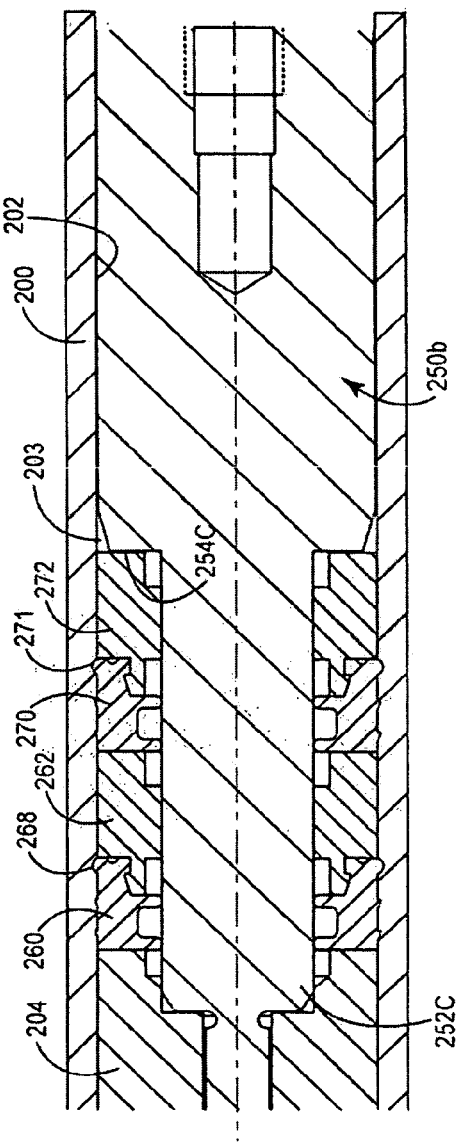

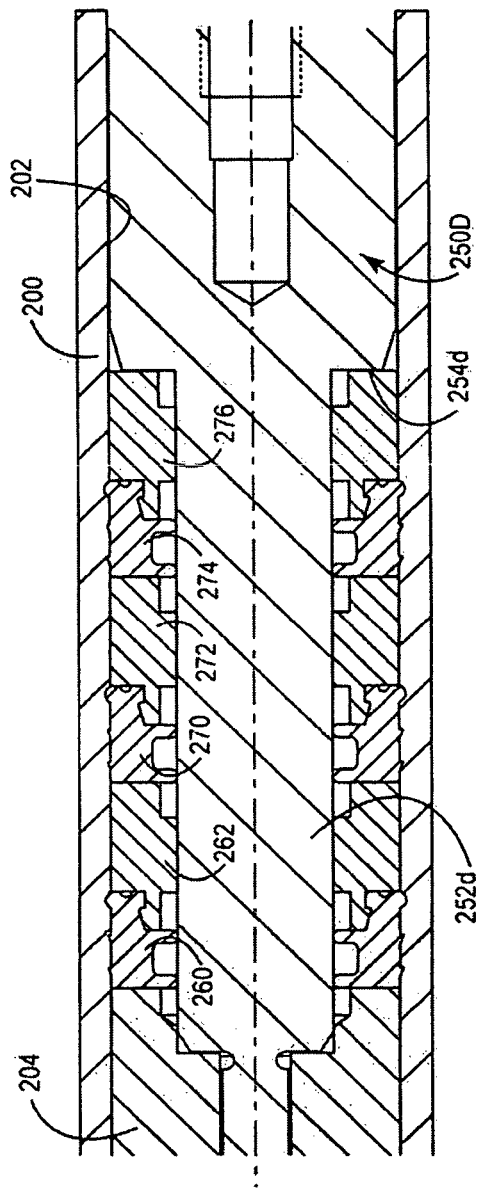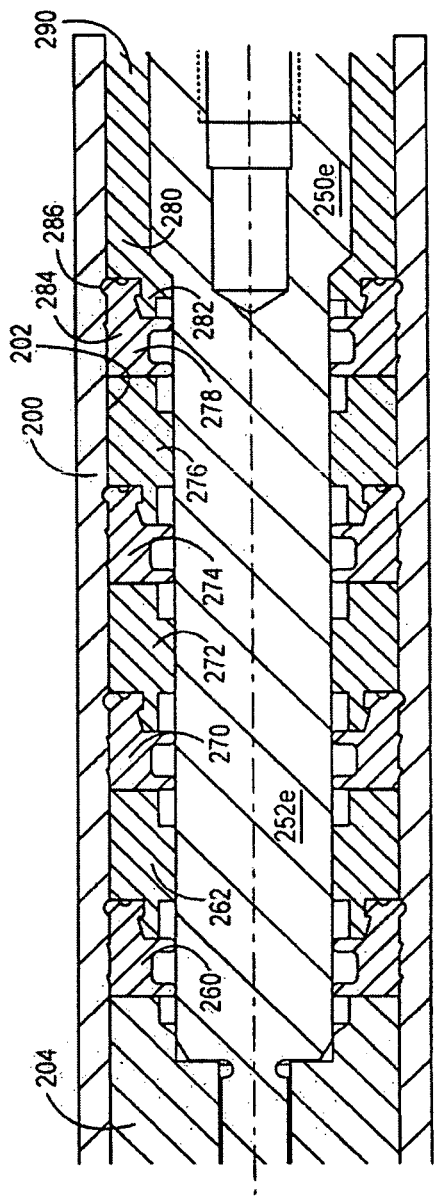

CONNECTOR ASSEMBLY WITH INTERNAL SEALS AND MANUFACTURING METHOD

CROSS-REFERENCE TO RELATED APPLICATION

The present non-provisional U.S. patent application is a continuation-in-part of prior non-provisional patent application having common title and filed on Dec. 7, 2006, and identified by application Ser. No. 11/608,011.

TECHNICAL FIELD

The invention relates generally to implantable medical device connector assemblies and in particular to a device connector assembly including internal seals and an associated method of manufacture.

BACKGROUND

Electrical connectors and other similar electrical components often include electrical conductors embedded within an insulating block to isolate the conductor from the surrounding environment. Embedding the conductor within a block protects the conductor and prevents the delivery of an unintended electrical shock. Electrical connector assemblies are coupled to a hermetically sealed housing of an implantable medical device (IMD) that encloses internal circuitry such as a hybrid circuit board and one or more batteries. Such a medical device connector assembly is adapted for receiving medical leads used with the implantable medical device.

Methods for forming electrical connector assemblies having conductors embedded within an insulating block may include injection molding techniques or thermoset casting techniques. An improved method for forming an implantable medical device connector assembly with embedded conductors is generally disclosed in U.S. Pat. No. 6,817,905 (Zart et al.), hereby incorporated herein by reference in its entirety. The method generally includes forming a core portion using either an injection molding process or a machining process. The core portion is fitted with electrically conductive components and submitted to a subsequent overmold process in which a second shot of thermoplastic material is injected into the mold. This process allows complex connector structures to be manufactured in a fast production cycle.

In the implantable medical device industry, standards have been developed for lead connector assemblies which are adapted to mate with the device connector assembly. In past practice, lead connector assemblies have included sealing members positioned around insulating structures located between lead connector terminals. The sealing members prevent the ingress of body fluids into a connector bore thereby electrically isolating the connector circuit elements. Ingress of body fluids may otherwise lead to a short circuit between separate connector circuits.

BRIEF DESCRIPTION OF THE DRAWINGS

FIGS. 7 through 11 are side sectional views of a device connector assembly illustrating one method for assembling a stacked subassembly in the connector bore of the device connector assembly shell.

DETAILED DESCRIPTION

In the following description, references are made to illustrative embodiments for carrying out the invention. It is understood that other embodiments may be utilized without departing from the scope of the invention. Unless otherwise indicated, drawing elements are not shown to scale.

Emerging lead connector assemblies, for example assemblies commonly referred to as "IS4" connector assemblies, include in-line lead terminals that are separated by insulating structures but do not include sealing members for forming a fluid-tight seal within a device connector assembly. A device connector assembly adapted to receive such a lead connector assembly should therefore incorporate sealing members within the connector bore to provide electrical isolation of the connector circuits. Such sealing members are typically formed as rings fabricated from a supple, biocompatible material, such as silicone rubber. The sealing members are adapted to mate with insulating structures of the lead connector assembly to form a fluid-resistant seal.

Figure 1:
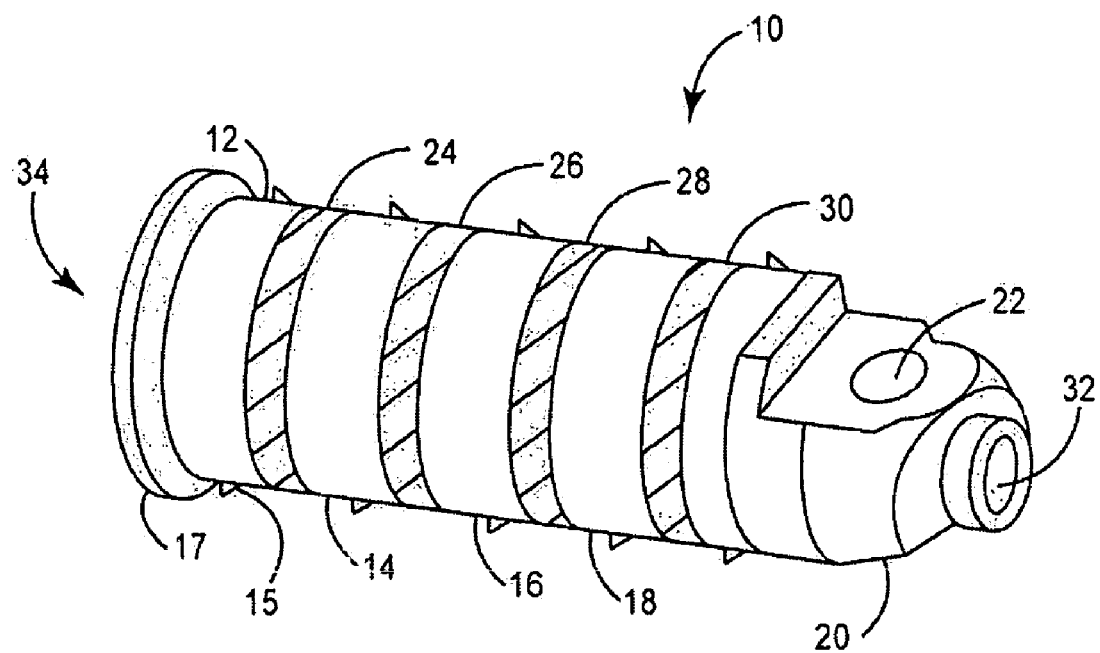
FIG. 1 is a perspective view of a subassembly of conductive connector members separated by sealing members.

FIG. 1 is a perspective view of a subassembly of conductive connector members separated by sealing members. The connector/sealing member subassembly 10, referred to hereafter as "stacked subassembly", is used in assembling an implantable medical device connector assembly. Stacked subassembly 10 includes an end cap 12 and four conductive connectors 14, 16, 18 and 20, also referred to herein as conductive members, separated by sealing members 24, 26, 28 and 30 in a "stacked" configuration. Connector 20 is adapted for receiving a lead pin terminal (not shown) and includes an open end aperture 32 through which a pin terminal of a lead connector assembly may be inserted. Connector 20 is shown embodied as a set screw block and further includes a set screw aperture 22 for receiving a set screw (not shown) used for securing the pin terminal of a lead connector assembly to retain the lead connector assembly within a connector bore formed by stacked subassembly 10. Connector 20 may alternatively be embodied as a spring contact or other contact adapted for receiving and engaging a lead pin terminal.

The remainder of the connectors 14, 16, and 18 may be embodied as multi-beam contacts, spring contacts, or any other suitable electrical contacts for making electrical connection with lead connector terminals that become aligned with connectors 14, 16, and 18 when the lead connector assembly is fully inserted into stacked subassembly 10.

End cap 12 is provided with an open receptacle 34 for receiving a lead connector assembly and acts to terminate the stack and retain the stack within a device connector assembly. End cap 12 is generally formed of a rigid material which may be conductive or non-conductive. End cap 12 may include a radial flange 17 extending outward from the stacked subassembly components to define the receptacle 34. As used herein, the term "distal" used with reference to a stacked subassembly for use in a device connector assembly refers to a direction corresponding to end cap 12 and open receptacle 34. The term "proximal" as used herein with reference to the device connector assembly refers to a direction corresponding to connector 20 for engaging a proximal lead connector pin.

One or more of end cap 12 and connectors 14, 16, 18 and 20 may be provided with an outer retention member 15 extending along an outer surface of the respective end cap 12 or connectors 14 through 20. Retention member 15 is shown as a barb or ridge that slides into a connector bore formed by in a connector assembly shell (as will be further described below) and subsequently engages the inner surface of the connector assembly shell to prevent slippage or removal of stacked subassembly 10 from the connector bore. Other engaging mechanisms may be implemented as surface features on the rigid components of stacked subassembly 10, namely end cap 12 and connectors 14 through 20, to mechanically secure stacked subassembly 10 within a connector bore.

Sealing members 24, 26, 28 and 30 are fabricated from an insulating material to electrically isolate connectors 14, 16, 18 and 20. Sealing members 24, 26, 28 and 30 are typically formed of a resilient material, such as a medical grade silicone rubber, such that sealing members 24, 26, 28 and 30 form a fluid-resistant seal with insulating structures of a lead connector. When the lead connector is fully inserted into stacked subassembly 10, which has been assembled in an IMD connector assembly, sealing members 24, 26, 28, and 30 will be aligned with insulating structures separating lead connector terminals. An inner surface of sealing members 24, 26, 28 and 30 will form a fluid-resistant interface with the insulating structures of the lead connector assembly, thereby preventing body fluids from creating a short circuit between lead terminals and stacked subassembly connectors 14, 16, 18, and 20.

Figure 2:
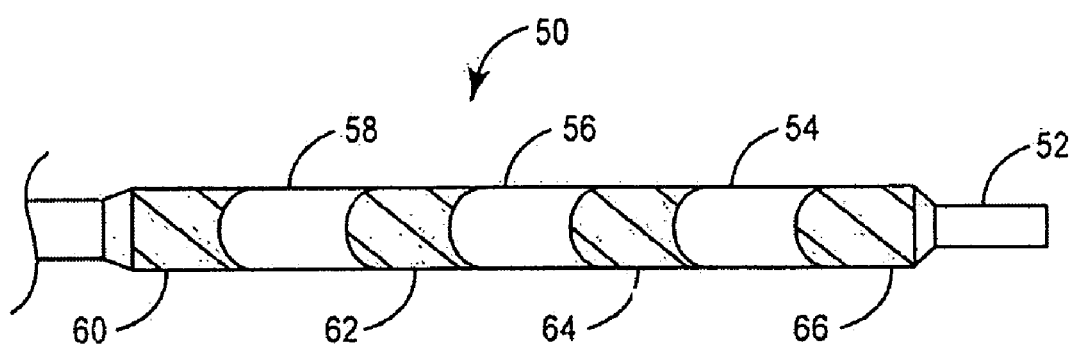
FIG. 2 is a plan view of a proximal lead connector assembly adapted for use with the stacked subassembly of FIG. 1.

FIG. 2 is a plan view of a proximal lead connector assembly adapted for use with the stacked subassembly of FIG. 1. Lead connector assembly 50 includes a pin connector terminal 52 and three ring connector terminals 54, 56, and 58. Lead connector assembly 50 may generally correspond to an IS4 connector assembly, having four inline terminals 52, 54, 56 and 58, however embodiments of the invention may be adapted for use with other lead connector assembly configurations. Each of terminals 52, 54, 56, and 58 are electrically coupled to respective insulated conductors extending through an elongated lead body to electrodes generally positioned along the distal end of the lead body. The terminals 52, 54, 56, and 58 are separated and electrically isolated from one another by insulating structures 60, 62, 64, and 66. Lead connector assembly 50 is commonly referred to as an "in-line" connector assembly in contrast to bifurcated connector assemblies which carry connector terminals on separate branches. In past practice, in-line lead connector assemblies typically have included sealing rings along the insulating structures between connector terminals for providing a fluid resistant seal between circuit elements when the lead connector assembly is coupled to an implanted device. Lead connector assembly 50 does not include such sealing rings. Embodiments of the invention include device connector assemblies adapted to receive any in-line lead connector assembly, particularly in-line lead connectors that do not incorporate sealing rings on the lead connector.

Figure 3:
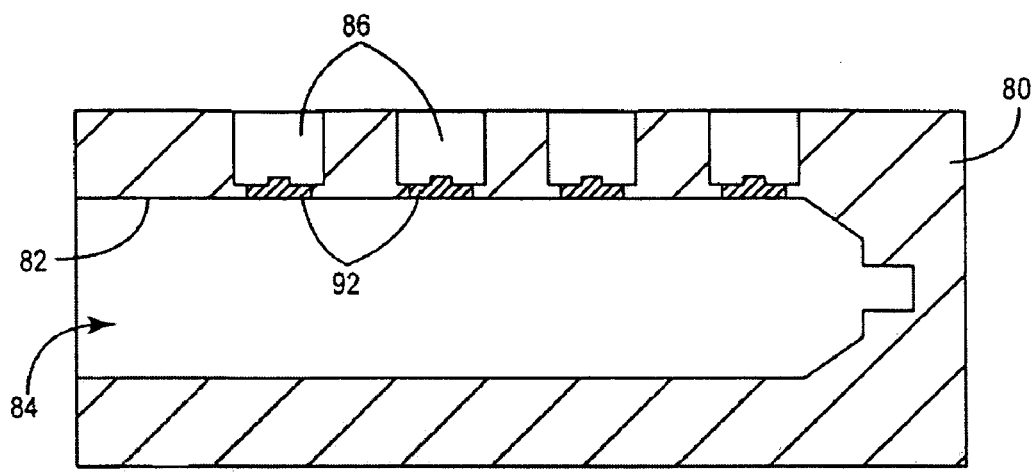
FIG. 3 is a side sectional view.
Figure 4:
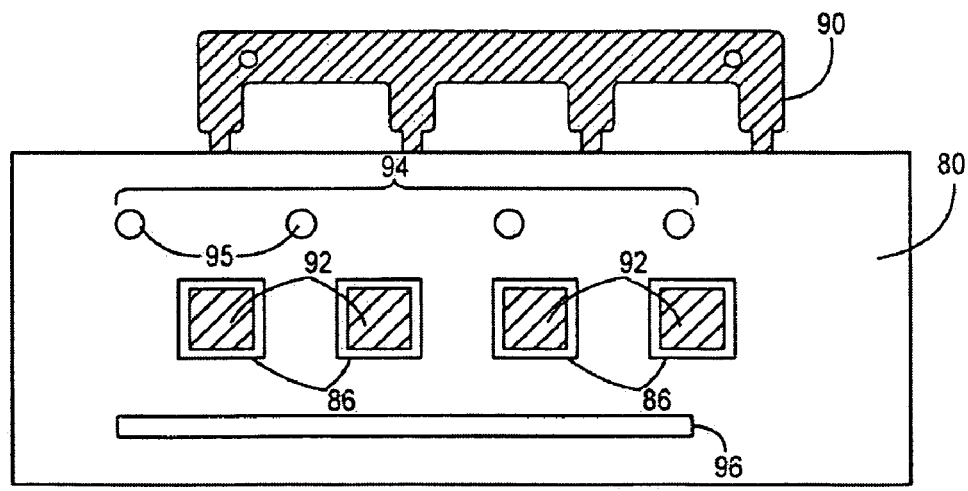
FIG. 4 is a top view of a connector assembly shell according to one embodiment of the invention.

FIG. 3 is a side sectional view and FIG. 4 is a top view of a connector assembly shell according to one embodiment of the invention. Shell 80 is formed during a casting or molding process. Shell 80 may be formed from a thermoplastic material, such as a polyurethane, and may thus be formed during high pressure and/or high temperature processes. Suitable polyurethane materials for forming shell 80 include a 75D polyurethane such as Thermedics™ Tecothane® available form Noveon, Inc., Cleveland, Ohio, or Pellethane™ available from Dow Chemical, Midland, Mich. Shell 80 is fabricated by loading a mandrel (not shown) and a circuit member 90 in a mold into which the thermoplastic material is applied. Shell 80 is thereby formed having an inner surface 82, which is formed by the mandrel, defining a connector bore 84. Circuit member 90 is embedded in molded shell 80 such that multiple traces 92 are stably positioned and exposed along connector bore 84. Traces 92 will be subsequently electrically coupled to connectors included in a stacked subassembly that will be positioned along connector bore 84. Circuit member 90 is trimmed during manufacturing methods to electrically separate traces 92 and form electrically-isolated conductor paths.

Shell 80 is shown in FIGS. 3 and 4 having a single circuit member represented by circuit member traces 92 and a single connector bore 84, however it is recognized that a connector shell may be formed having multiple connector bores to allow connection of more than one lead to the associated IMD. Other connector bores may include connector components assembled in the mold which become embedded in shell 80 in an overmolding process, for example as described in the '905 Zart patent.

Shell 80 is formed having multiple windows 86 aligned with circuit member traces 92, visible within windows 86. Windows 86 provide access for electrically coupling traces 92 to connectors included in the stacked subassembly positioned in connector bore 84. Shell 80 optionally includes a fill port 95, which may include multiple apertures 94 each corresponding to a sealing member location with shell 80. In some embodiments, fill port 95 may be used for delivering an adhesive for creating a bond between shell inner surface 82 and sealing members included in a stacked subassembly inserted in connector bore 84. Such adhesive bonding is optional and may be used to provide a redundant seal in the completed connector assembly. When fill port 95 is included, an over fill port 96 is provided to allow excess adhesive and air bubbles to escape during the delivery process. As will be described herein, an adhesive bonding is not required for creating a fluid-resistant seal between sealing members included in a stacked subassembly and inner surface 82. As such, shell 80 may be formed without fill port 95 and over fill port 96.

In alternative embodiments, circuit member 90 may be assembled with shell 80 after molding shell 80. Shell 80 may be formed with channels, grooves, recesses or other features for receiving, retaining and/or aligning conductive traces of circuit member 90. Shell 80 may additionally include other embedded components or be formed with other additional features for receiving components during an assembly process, depending on the particular application.

Figure 5:
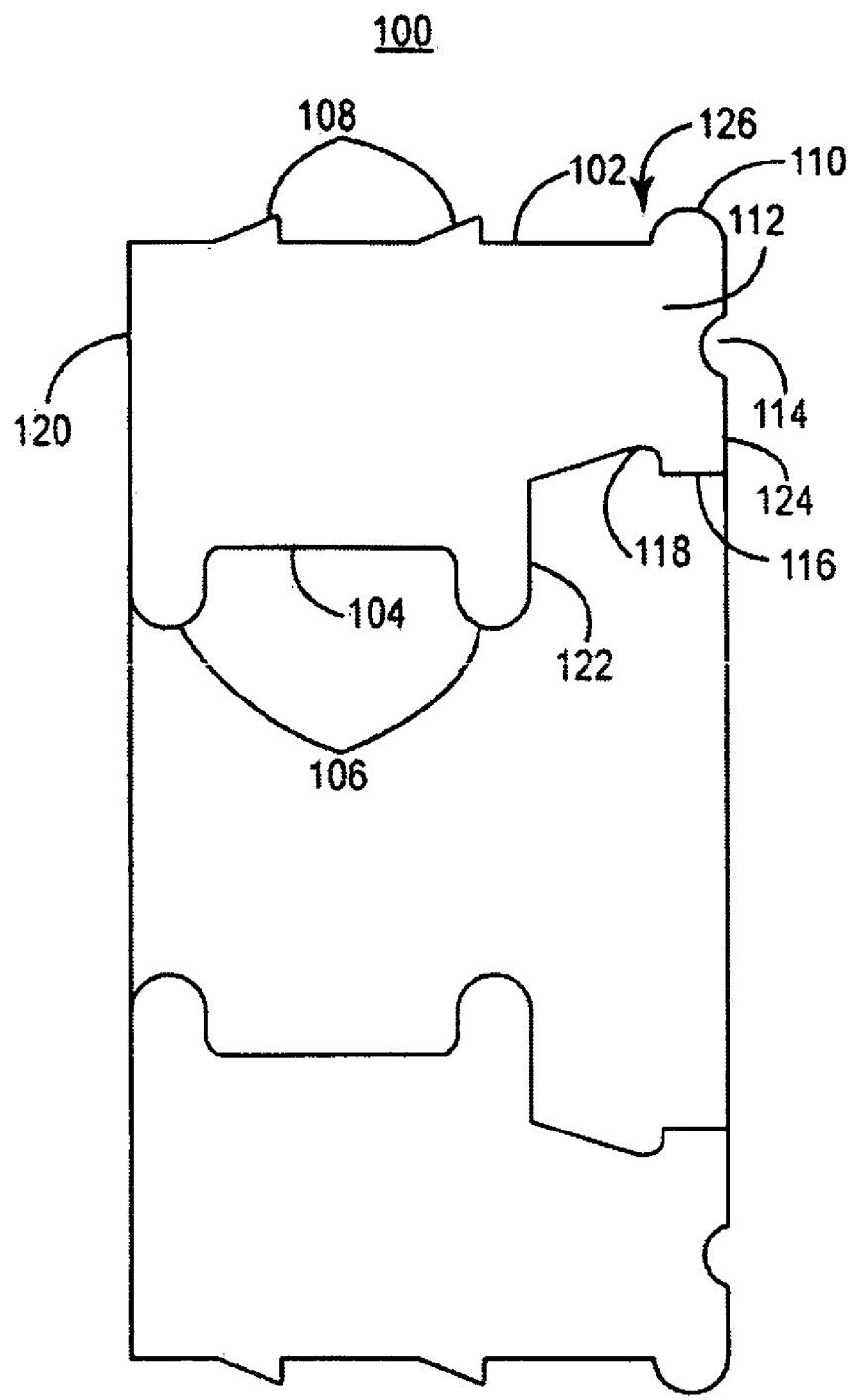
FIG. 5 is a side sectional view of a sealing member for use in a device connector assembly according to one embodiment of the invention.

FIG. 5 is a side sectional view of a sealing member for use in a device connector assembly according to one embodiment of the invention. Sealing member 100 is a molded component formed from a solid piece of a resilient material such as silicone rubber. Sealing member 100 is generally cylindrical having an outer surface 102 and an inner surface 104 extending between a proximal face 120 and a distal face 122. Proximal face 120 and distal face 122 will be positioned against adjacent connector components in a stacked subassembly.

One or more inner sealing rings 106 protrude radially inward from inner surface 104 to interfere with an insulating member included in a lead connector assembly, thereby forming a fluid resistant seal with the insulating member. At least one outer sealing ring 110 protrudes radially outward from outer surface 102 to interfere with the inner surface of the shell connector bore, thereby forming a fluid resistant seal with the shell inner surface. Additional minor interference members 108 may optionally be included. Minor interference members 108 extend radially outward from outer surface 102 and interfere with the inner surface of the shell connector bore. Minor interference members 102 when present, facilitate centering of the stacked subassembly components upon assembly within the shell connector bore and provide redundant seals between sealing member 110 and the shell connector bore.

Sealing member 110 includes a flange 112 extending axially from distal face 122 and forming a portion of the outer surface 102. The axially-extending flange 112 includes an inner surface 116 for mating with an adjacent connector component. Inner surface 116 may be provided with a groove 118 or other feature to promote a stable, interlocking interface between sealing member 100 and the adjacent connector component when assembled in a stacked subassembly. Outer sealing ring 110 is provided along a portion 126 of outer surface 102 corresponding to flange 112. Flange 112 may be provided with a compression groove 114 along flange distal face 124 to allow radial compression of sealing member 110 to occur thereby preventing a locking up of components when sealing member 100 is fitted within the shell connector bore. It is recognized that other designs may provide for compressibility of outer sealing ring 110 by removing a portion of the solid material forming flange 112 for forming a compression feature that prevents a "hydraulic lock" of the sealing member 110 within the shell connector bore while still allowing a fluid-resistant seal to be formed between the outer sealing ring 110 and the shell connector bore without axial compression of sealing member 110. It is further contemplated that a compression feature may be included in the shell or in an adjacent connector flange. This compression feature, whether in the seal material or the adjacent structures, facilitates effective sealing over a larger range of connector bore tolerances.

Figure 6:
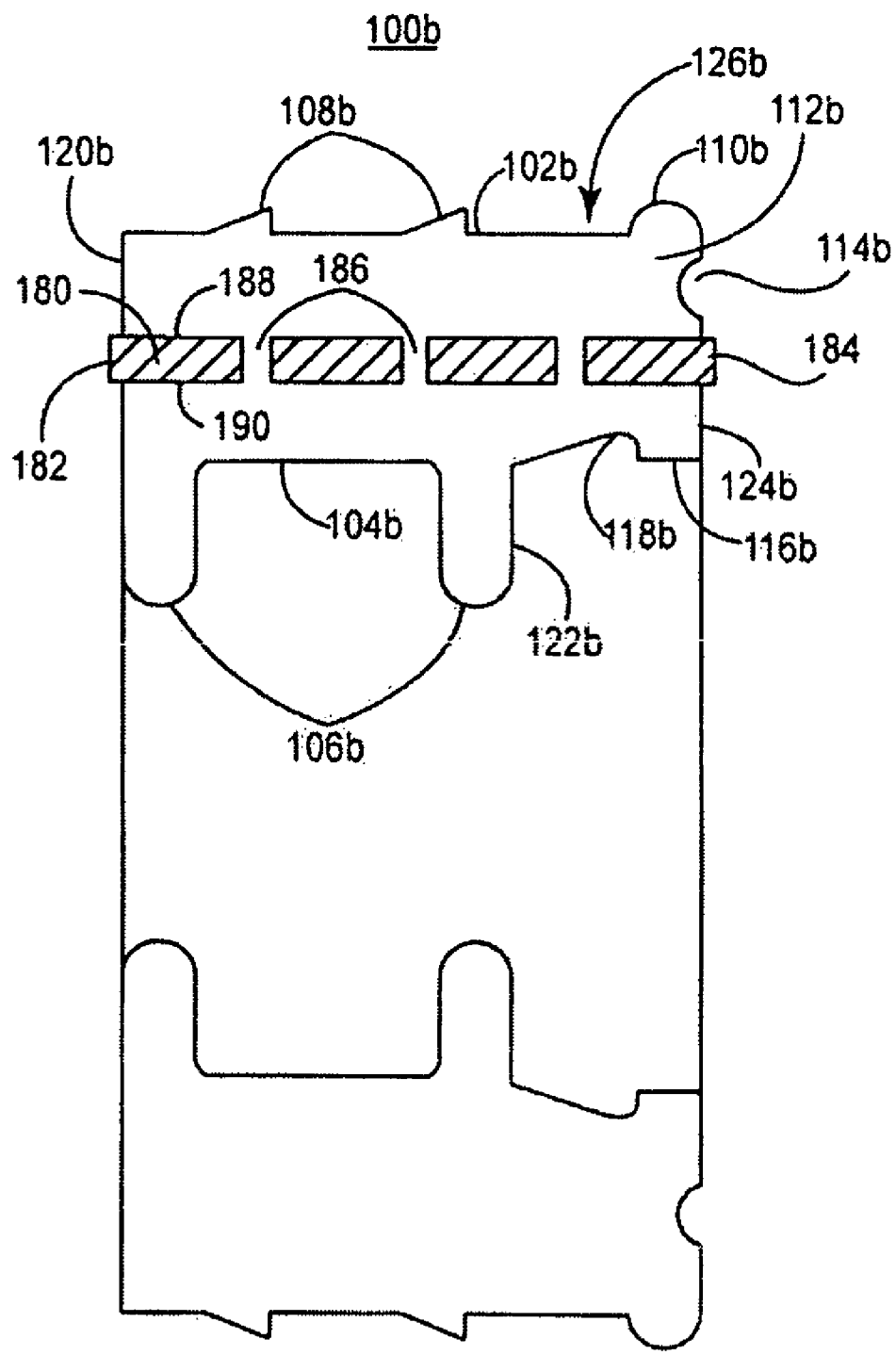
FIG. 6 is a side sectional view of a sealing member according to an alternative embodiment of the invention.

FIG. 6 is a side sectional view of a sealing member according to an alternative embodiment of the invention. Like features of sealing member 100b as compared to sealing member 100 of FIG. 5 are designated with like numeric identifiers including an additional suffix. Sealing member 100b includes a rigid support member 180 extending axially through sealing member 100b between proximal face 120b and flange distal face 124b. Sealing member 100b is formed by molding a resilient material such as silicone rubber onto rigid support member. Rigid support member is formed from a rigid, insulating material, which may be, for example, any of the materials listed previously for forming the shell 80 shown in FIG. 3. Rigid support member 180 may include one or more through holes 186 which allow the molded sealing member 100b to be continuous both above (the portion forming outer surface 102b) and below (the portion forming inner surface 104b) support member 180.

Rigid support member 180 includes an outer surface 188 and an inner surface 190 extending between a proximal end 182 and a distal end 184. Proximal end 182 may be flush with proximal face 120b of sealing member 100b or may protrude beyond proximal face 120b as shown in FIG. 6. Likewise, distal end 184 may be flush with flange distal face 124b or may protrude beyond flange distal face 124b as shown in FIG. 6. Rigid member 180 provides axial support to sealing member 100b during an assembly process in which sealing member 100b is assembled within the shell connector bore with other stacked subassembly components. Rigid member 180 may also acts to prevent axial compression of sealing member 100b such that stacked subassembly components maintain a precise location within the shell connector bore. As will be further described herein, the formation of a fluid-tight seal between outer sealing ring 110b and the inner surface of the shell connector bore does not rely on axial compression of sealing member 100b. As such, rigid member 180 may be included in sealing member 100b to provide axial support of sealing member 100b.

Figure 7:
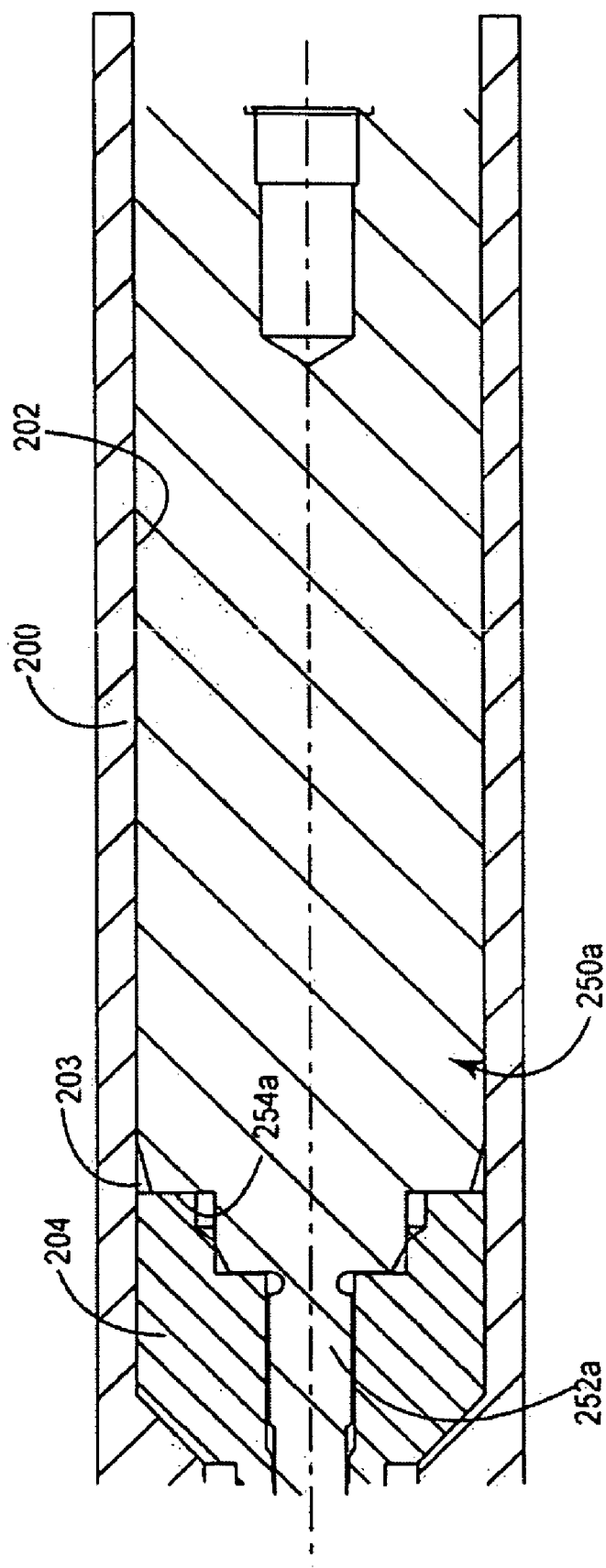

FIGS. 7 through 11 are side sectional views of a device connector assembly illustrating one method for assembling a stacked subassembly in the connector bore of the device connector assembly shell. The components of the stacked subassembly are positioned along connector bore 203 using multiple assembly tools having calibrated lengths for accurate positioning. In FIG. 7, a connector assembly shell 200 is shown having an inner surface 202 forming the connector bore 203. A connector component 204, embodied as a set screw block, is mounted on an assembly tool 250a having a distal mandrel 252 on which the connector component 204 is mounted. The axial length of mandrel 252a extending from proximal face 254a of tool 250a corresponds to the axial length of connector component 204 such that connector component 204 is accurately placed at the proximal end of the connector bore 203.

In FIG. 8, a first pair of stacked subassembly components including sealing member 260 and connector 262 is assembled in connector bore 203 using assembly tool 250b. Tool 250b has a mandrel 252b extending from proximal face 254b. Sealing member 260 and connector 262 are mounted on mandrel 252b such that when mandrel 252b is fully inserted into connector bore 203, sealing member 260 and connector 262 are positioned adjacent connector 204. Connector 262 includes an axially-extending flange 264 having an outer surface 265 configured to mate with an inner surface 258 of axially-extending flange 266 of sealing member 260. Connector flange 264 may be provided with a mating feature 257 to interlock or mate with a corresponding feature 259 of sealing member flange 266. In the embodiment shown, connector flange 264 includes a ridge 257 for mating with a groove 259 provided along sealing member flange 266.

The axially-extending flange 266 of sealing member 260 is positioned between the inner surface 202 of shell 200 and the outer surface 265 of connector flange 264. In this way, sealing ring 268 and sealing member flange 266 become compressed in a radial direction between shell inner surface 202 and connector flange outer surface 265. The interference between sealing ring 268 and inner surface 202 creates a fluid-resistant seal between the proximal connector 204 and connector 262. Compression groove 269 allows radial compression of flange 266 to prevent locking up of the sealing member 260 within the connector bore. The fluid-resistant seal formed between sealing member 266 and inner surface 202 is accomplished without the use of an adhesive and without axial compression of sealing member 260.

FIG. 9 illustrates the assembly step for placing a second pair of stacked subassembly components within connector bore 203. Sealing member 270 and connector 272 are inserted into bore 203 using assembly tool 250c. Sealing member 270 and connector 272 are mounted on mandrel 252c extending from proximal face 254c of tool 250c and positioned adjacent connector 262 such that a fluid-resistant seal is formed between inner surface 202 of shell 200 and sealing ring 271 in the same manner as described above. Mandrel 252c is provided with a length corresponding to the axial positions of sealing member 270 and connector 272 along connector bore 203 to facilitate accurate positioning of sealing member 270 and connector 272 along connector bore 203. In FIG. 10, a third pair of stacked subassembly components, sealing member 274 and connector 276, are inserted into bore 203 using assembly tool 250d. Sealing member 274 and connector 276 are mounted on mandrel 252d of tool 250d and assembled in connector bore 203.

Finally, sealing member 278 and end cap 280 are mounted on mandrel 252e of assembly tool 250e and assembled in connector bore 203 adjacent connector 276 as shown in FIG. 11. End cap 280 includes an axially-extending flange 282 for interfacing with sealing member flange 284. The interference between shell inner surface 202 and sealing ring 286 provides a fluid-resistant seal near connector bore receptacle 290. End cap 280 may form a press fit within the distal portion of connector bore 203 to mechanically lock within bore 203 and may include retention members implemented as outer surface features formed on end cap 280, as described previously in conjunction with FIG. 1 for interfacing/interlocking with shell inner surface 202. In alternative embodiments, end cap 280 and inner surface 202 may be threaded such that end cap 280 may be screwed into bore 203. In still other embodiments, end cap 280 may be bonded within bore 203 using welding, adhesives or other appropriate bonding method.

Connectors 204, 262, 272, 276 and end cap 282 may be dimensioned and/or include outer surface features for interfacing with shell inner surface 202 to create a mechanical lock with shell inner surface 202. In one embodiment, connectors 204, 262, 272, 276 and end cap 282 include retention members as shown previously in FIG. 1 (not shown in FIGS. 7-11). In other embodiments, inner surface 202 may be formed such that connector bore 203 is provided with a variable diameter along its length corresponding to varying diameters of stacked assembly components. For example, inner surface 202 may be provided with a step-like, increasing diameter wherein a smallest diameter is provided in the proximal portion of connector bore 203 corresponding to the location of connector 204 and a largest diameter being provided in the distal portion of connector bore 203 corresponding to the location of end cap 282 with connectors 204, 262, 272, 276 and end cap 282 formed having corresponding diameters.

While sealing members 260, 270, 274 and 278 are shown having flanges extending in the distal direction to interface with connectors 262, 272, 276 and end cap 280 having flanges extending in the proximal direction, it is recognized that alternative embodiments could include sealing members 260, 270, 274 and 278 having proximally-extending flanges for mating with connectors 204, 262, and 272 and 276 having flanges extending in a distal direction. The drawings provided herein illustrate various embodiments for incorporating the sealing members within a connector bore. It is recognized that one having skill in the art and the benefit of the teachings provided herein could conceive of alternative configurations and geometries of sealing members and connectors wherein the sealing member is adapted to form a seal with the shell inner surface without requiring axial compression of the sealing member and without requiring the use of an adhesive.

Figure 12:
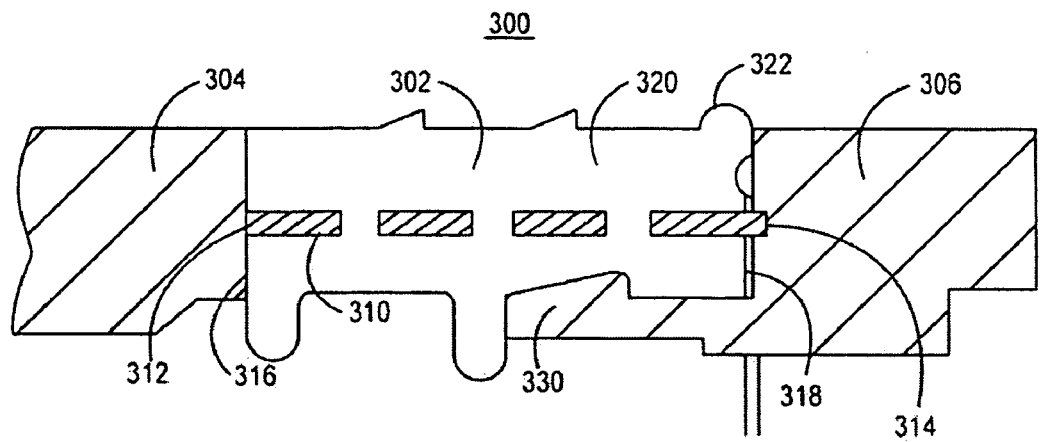
FIG. 12 is a partial side sectional view of a sealing member assembled in a stacked subassembly with connector members.

FIG. 12 is a partial side sectional view of a sealing member assembled in a stacked subassembly with connector members. Stacked subassembly 300 includes sealing member 302 assembled between two connectors 304 and 306. Sealing member 302 includes a rigid support member 310 extending between sealing member proximal face 316 and sealing member flange distal face 318. Rigid support member 310 has a proximal end 312 shown to be substantially flush with proximal face 316 and a distal end 314 extending beyond distal face 318. It is recognized that rigid support member 310 may be configured such that either or both of proximal end 312 and distal end 314 terminate within sealing member 302, substantially flush with the respective proximal face 316 or distal face 318, or beyond the respective proximal face 316 or distal face 318. Rigid support member 310 provides axial support to sealing member 302 during assembly within the shell connector bore. Rigid support member 310 restricts axial compression of sealing member 302 thereby maintaining the shape of sealing member 302 as it is assembled within the connector bore. Sealing ring 322 extending along flange 320 forms a fluid tight seal when positioned between connector flange 330 and the shell connector bore inner surface (not shown) as described previously. By providing axial support to sealing member 302, an complete stacked subassembly may be inserted into a shell connector bore in one step rather than in multiple steps as described above in conjunction with FIGS. 7-11 without significant deformation of sealing member 302.

Figure 13:
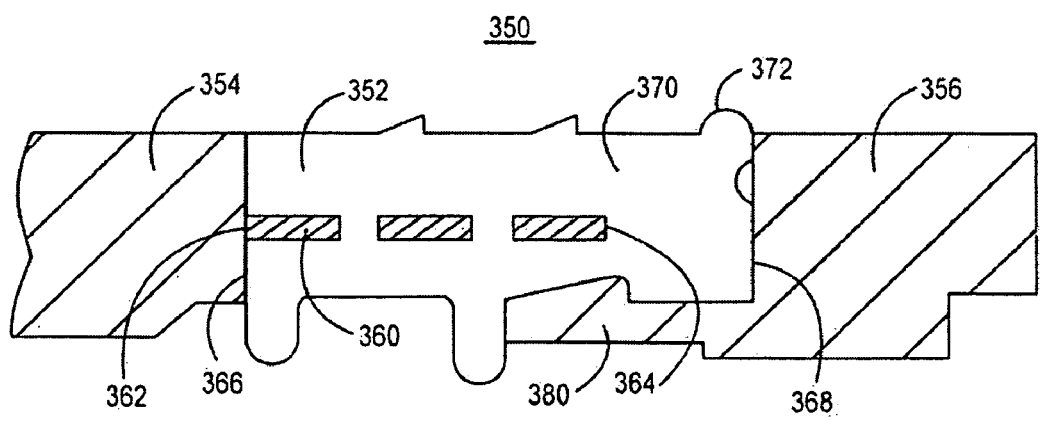
FIG. 13 is a partial side sectional view of an alternative embodiment of a stacked subassembly including sealing members having rigid support members.

FIG. 13 is a partial side sectional view of an alternative embodiment of a stacked subassembly including sealing members having rigid support members. Stacked subassembly 350 includes a sealing member 352 assembled between two connectors 354 and 356. Sealing member 352 is provided with a rigid support member 360 extending from a proximal end 362 positioned flush with sealing member proximal face 366 to a distal end 364 terminating within sealing member 352, prior to flange distal face 368. Rigid member 360 provides axial support to sealing member 352 while allowing radial compression of sealing member flange 370 between the shell inner surface (not shown in FIG. 13) and flange 380 of connector 356. Sealing ring 372 is thereby pressed against the shell inner surface to form a fluid-resistant seal.

Figure 14:
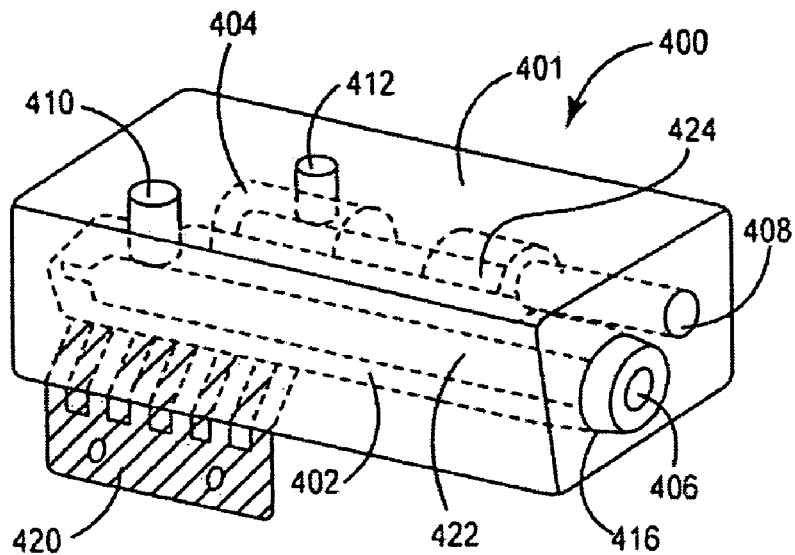
FIG. 14 is a perspective view of a device connector assembly including a molded shell and stacked subassembly inserted into the bore of the molded shell according to one embodiment of the invention.

FIG. 14 is a perspective view of a device connector assembly including a molded shell and stacked subassembly inserted into the bore of the molded shell according to one embodiment of the invention. Connector assembly 400 includes molded shell 401 formed during an overmolding process to partially embed circuit member 420. A stacked subassembly 402 is inserted into connector bore 422, indicated by dashed line, having receptacle 406 in end cap 416 for receiving a lead connector assembly. Connector assembly 400 may further include one or more additional receptacles for receiving additional leads in one or more additional connector bores. In the example shown, connector assembly 400 includes a second receptacle 408 for receiving a lead inserted into a second connector bore 424. Shell 401 may encapsulate connectors 404 positioned in the mold during the overmolding process, along the second connector bore 424. In the embodiment shown, circuit member 420 includes traces extending to connectors included in stacked subassembly 402 along connector bore 422 and to the overmolded connectors 404 included along connector bore 424. Thus, connector assembly 400 may include multiple connector bores, which may further include any combination of overmolded connectors and connectors inserted as stacked subassemblies into the connector bore after molding connector shell 401.

Connector assembly 400 includes a set screw aperture 410 for receiving a set screw advanced into a set screw block positioned along connector bore 422. Connector assembly 400 may include additional set screw apertures 412 as needed for receiving additional set screws used for securing lead connector assemblies positioned in other connector bores 424. Connector assemblies may alternatively be fabricated with other connectors in place of set screw blocks, such as spring connectors, for receiving lead connector pins, thereby eliminating the need for set screw apertures.

Figure 15:
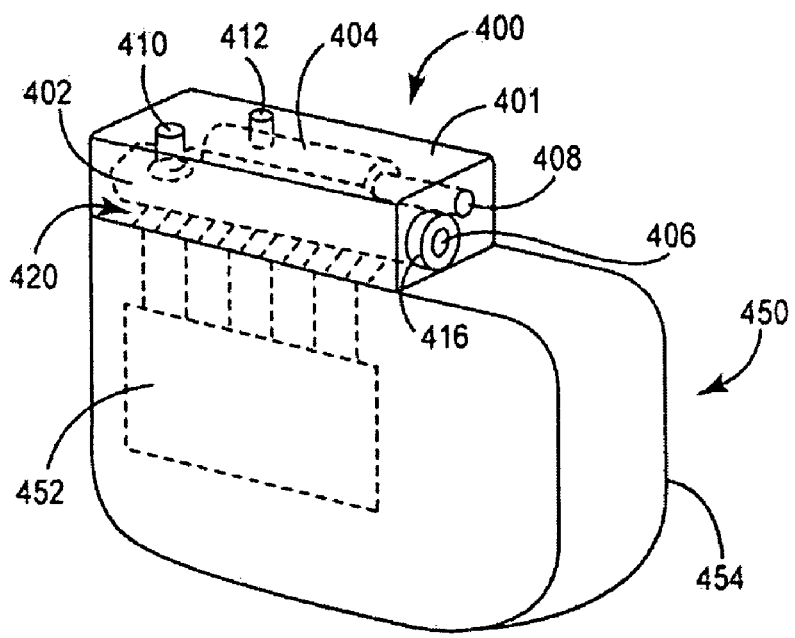
FIG. 15 is a perspective view of the completed connector assembly 400 shown in FIG. 14 coupled to an IMD.

FIG. 15 is a perspective view of the completed connector assembly 400 shown in FIG. 14 coupled to an IMD 450. IMD 450 may be a pacemaker, cardioverter/defibrillator, neurological stimulator, physiological monitor, or any other implantable medical device utilizing medical leads. In particular, sealing members are provided along a stacked subassembly 402 for creating a fluid-resistant seal with insulating portions of a lead connector assembly inserted into receptacle 406. The sealing members also form a fluid-resistant interface with the inner surface of shell 401 along the outer surface of the sealing members as described herein. Stacked subassembly 402 is assembled on an insertion tool(s) and assembled into connector shell 401 in one or more insertion steps after shell 401 has been molded. Circuit member 420, partially embedded in connector shell 401, has been trimmed and electrically connected to internal circuitry 452 enclosed in IMD housing 454. Electrical connection between IMD internal circuitry 452 and circuit member 420 is typically made via a feedthrough array extending through hermetically sealed housing 454.

Figure 16:
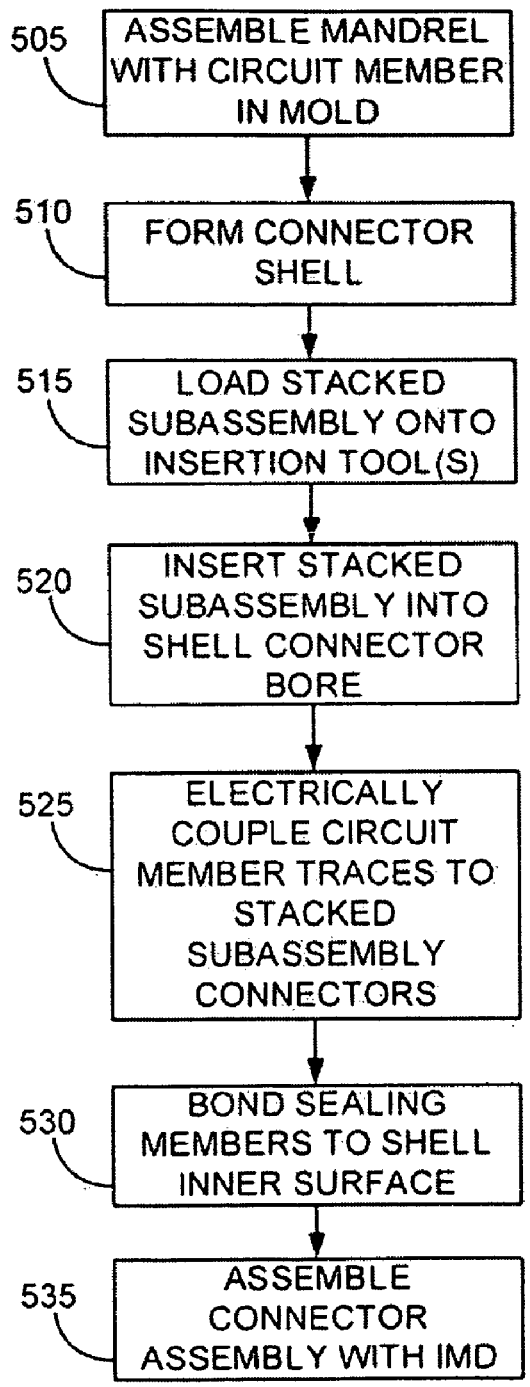
FIG. 16 is a flow chart summarizing steps included in an assembly method according to one embodiment of the invention.

FIG. 16 is a flow chart summarizing steps included in an assembly method according to one embodiment of the invention. Method 500 includes assembling a mandrel in a mold for forming a connector shell at block 505. The connector shell is molded at block 510, typically using a thermoplastic material such as polyurethane in a high temperature, high pressure process. A shell inner surface is formed by the mandrel defining a connector bore. The shell may further include other features such as windows for electrically coupling a circuit member to connectors positioned in the connector bore, a fill port for optionally injecting adhesive for bonding the shell inner surface with the outer surface of sealing members positioned in the connector bore, set screw apertures, and other features for accommodating additional connector bore circuit members, connectors, or other components to be included in the connector assembly. As described previously, the circuit member may be assembled in the mold at block 505, prior to injecting the shell material, such that portions of the circuit member are embedded in the molded shell.

At block 515, a stacked subassembly including sealing members, connectors and an end cap, which may be provided with interlocking features, are loaded onto an insertion tool or a set of tools having calibrated mandrel lengths. Using the tool(s), the stacked subassembly is inserted into the shell connector bore at block 520, either as a complete stack or in sections. Retention members may be provided along the stacked subassembly for engaging the shell inner surface and securing the stacked subassembly within the connector bore upon full insertion. As described above in conjunction with FIGS. 7-11, the insertion step performed at block 520 may include multiple steps of mounting pairs of sealing members and connectors on each one of a set of assembly tools having calibrated mandrel lengths for precise positioning of the sealing member/connector pairs along the shell connector bore.

The individual traces of the circuit member are electrically coupled to the stacked subassembly connectors at block 525. Electrical coupling between circuit member traces and subassembly connectors may be performed through windows included in the connector shell and may involve welding, or application of conductive adhesives. Electrical coupling between traces and connectors may additionally or alternatively include mechanical coupling between the traces and connectors involving riveting, staking, crimping or a protruding mechanical coupling member such as a spring, barb, button, or beam.

At block 530, an optional step of injecting a thermoset material into fill ports provided in the connector shell may be performed to bond the outer surface of the sealing members included in the stacked subassembly to the shell inner surface. Adhesive bonding may be used to provide redundant sealing between the sealing members and the shell inner surface but is not necessary. The connector assembly is assembled with an IMD at block 535, which may include trimming of the circuit member to separate individual circuit member traces.

Thus, an electrical medical device connector assembly incorporating sealing members and an associated fabrication method have been presented in the foregoing description with reference to specific embodiments. It is appreciated that various modifications to the referenced embodiments may be made without departing from the scope of the invention as set forth in the following claims.

The invention claimed is:

1. An implantable medical device connector assembly adapted for receiving a medical electrical lead having a lead connector assembly, comprising:
   a molded, insulative shell having an inner surface forming a connector bore,
   a circuit member including a plurality of conductive traces extending through the shell; and
   a stacked subassembly positioned along the connector bore, the stacked subassembly having a bore opening adapted to receive a lead connector assembly comprising:
      a plurality of conductive members positioned along the connector bore and electrically coupled to the plurality of traces, each of the conductive members having a main body portion and a flange portion, the conductive member flange portion having a lower surface facing inwardly toward the bore opening and an opposing upper surface; and
      a plurality of sealing members, each sealing member being positioned between conductive members, each of the plurality of sealing members having a main body portion and a flange portion, and each of the sealing members defining an inner surface establishing a fluid-resistant interface with the lead connector assembly of a medical electrical lead and an outer surface establishing a fluid-resistant interface with the inner surface of the shell,
      wherein the body portion of each of the plurality of sealing members includes an inner sealing ring protruding radially from the sealing member inner surface and establishing an interference fit with a lead connector assembly inserted into the bore of the stacked subassembly,
      wherein the flange portion of each of the plurality of sealing members includes an outer sealing ring protruding radially from the sealing member outer surface and establishing an interference fit with the inner surface of the shell connector bore without axial compression of the sealing member when the stacked subassembly is placed within the connector bore, wherein the flange portion of each sealing member overlaps the flange portion of an adjacent conductive member so as to be internally supported from underneath by the conductive member flange portion, such that compressive force exerted on the outer sealing ring due to the interference fit established upon the stacked subassembly being placed within the connector bore does not subject the sealing member body portion or the inner sealing rings to a distorting force.

2. The connector assembly of claim 1 wherein each of the plurality of sealing members includes a compression groove along a distal face of the flange portion to allow for radial compression of the sealing member.

3. The connector assembly of claim 1 wherein each of the plurality of sealing members includes a proximal face and a distal face and a rigid support member having an outer surface and an inner surface extending between the proximal face and the distal face.

4. The connector assembly of claim 3 wherein the rigid support member extending beyond at least one of the proximal face and the distal face.

5. The connector assembly of claim 3 wherein the rigid support member having an end being flush with at least one of the proximal face and the distal face.

6. The connector assembly of claim 3 wherein the rigid support member comprises through holes extending from the rigid support member outer surface to the rigid support member inner surface.

7. The connector assembly of claim 3 wherein the rigid support member having an end terminating within the sealing member.

8. The connector assembly of claim 1 wherein the plurality of conductive members and the plurality of sealing members include interlocking structures for stabilizing the position of the sealing members between the conductive members.

9. An implantable medical device for receiving a lead connector assembly, comprising:

a hermetically sealed housing;

a circuit member including a plurality of conductive traces;

a molded, insulative connector shell disposed along the housing, the connector shell embedding a portion of each of the plurality of conductive traces and having an inner surface forming a connector bore, a plurality of conductive members positioned along the connector bore and electrically coupled to the plurality of traces, the conductive members defining a bore opening adapted to receive the lead connector assembly;

a plurality of sealing members positioned, each sealing member being positioned between adjacent conductive members, each of the plurality of sealing members having an outer surface defining a fluid-resistant interface with the inner surface of the shell and defining an inner surface establishing a fluid-resistant interface with a lead connector assembly inserted within the bore opening;

wherein each of the plurality of sealing members include a sealing ring protruding radially from the sealing member outer surface for forming the fluid resistant interface with the inner surface of the shell without axial compression of the sealing member;

means for providing support to each sealing member from beneath the sealing member inner surface in an area of the sealing member that is opposite the sealing ring, and internal circuitry enclosed in the housing and electrically coupled to the circuit member.

10. The medical device of claim 9 wherein the sealing member support providing means includes an axially-extending flange on a conductive member, the flange having a first surface; and wherein each of the plurality of sealing members has an axially-extending flange that overlaps the first surface of the conductive member flange of an adjacent conductive member, such that the sealing member flange is positioned between the first surface of the conductive member flange of an adjacent conductive member and the shell inner surface.

11. The medical device of claim 9 wherein each of the plurality of sealing members includes a compression groove along a distal face of the flange portion to allow for radial compression of the sealing member.

12. The medical device of claim 9 wherein each of the plurality of sealing members includes a proximal face and a distal face and a rigid support member having an outer surface and an inner surface extending between the proximal face and the distal face.

13. The medical device of claim 11 wherein the rigid support member extending beyond at least one of the proximal face and the distal face.

14. The medical device of claim 11 wherein the rigid support member having an end being flush with at least one of the proximal face and the distal face.

15. The medical device of claim 11 wherein the rigid support member comprises through holes extending from the rigid support member outer surface to the rigid support member inner surface.

16. The medical device of claim 11 wherein the rigid support member having an end terminating within the sealing member.

17. The medical device of claim 9 wherein the plurality of conductive members and the plurality of sealing members include interlocking structures for stabilizing the position of the sealing members between the conductive members.

* * * * *